(12) United States Patent
Groome et al.

(10) Patent No.: US 7,897,350 B2
(45) Date of Patent: Mar. 1, 2011

(54) IMMUNOLOGICAL ASSAY AND ANTIBODIES FOR ANTI-MULLERIAN HORMONE

(75) Inventors: Nigel Patrick Groome, Chipping Norton (GB); Mark Cranfield, Banbury (GB); Axel P. N. Themmen, Dordrecht (NL); Gopal V. Savjani, Nassau Bay, TX (US); Ketusha Mehta, League City, TX (US)

(73) Assignees: Beckman Coulter, Inc., Brea, CA (US); Oxford Brookes University, Oxford (GB)

( * ) Notice: Subject to any disclaimer, the term of this patent is extended or adjusted under 35 U.S.C. 154(b) by 1257 days.

(21) Appl. No.: 11/439,548

(22) Filed: May 24, 2006

(65) Prior Publication Data

US 2006/0275850 A1    Dec. 7, 2006

Related U.S. Application Data

(60) Provisional application No. 60/684,239, filed on May 24, 2005.

(51) Int. Cl.
| | |
|---|---|
| G01N 33/50 | (2006.01) |
| G01N 33/53 | (2006.01) |
| G01N 33/541 | (2006.01) |
| G01N 33/563 | (2006.01) |
| G01N 33/577 | (2006.01) |
| G01N 33/58 | (2006.01) |
| G01N 33/74 | (2006.01) |
| C07K 16/00 | (2006.01) |
| C07K 16/18 | (2006.01) |
| C07K 16/26 | (2006.01) |

(52) U.S. Cl. ...... 435/7.1; 435/7.9; 530/387.1; 530/387.9; 530/388.1; 530/388.24; 530/389.1; 530/389.2; 530/391.1; 530/391.3

(58) Field of Classification Search .................. None
See application file for complete search history.

(56) References Cited

U.S. PATENT DOCUMENTS

| | | | |
|---|---|---|---|
| 5,310,880 | A | 5/1994 | Donahoe et al. |
| 5,359,033 | A | 10/1994 | Cate et al. |
| 2003/0124620 | A1 | 7/2003 | Seifer et al. |

OTHER PUBLICATIONS

Al-Qahtani, et al., "Development of a sensitive enzyme immunoassay for Anti-Mullerian Hormone (AMH) and the evaluation of potential clinical applications in males and females", Clinical Endocrinology 63(3), 267-73 (2005).
Baarends, et al., "Anti-Mullerian Hormone and Anti-Mullerian Hormone Type II Receptor Messenger Ribonucleic Acid Expression in Rat Ovaries during Postnatal Development, the Estrous Cycle, and Gonadotropin-induced follicle growth", Endocrinology 136, 4951-4962 (1995).
di Clemente, et al, "Cloning, Expression, and Alternative Splicing of the Receptor for Anti-Mullerian Hormone", Molecular Endocrinology 8, 1006-1020 (1994).
Durlinger, et al., "Control of Primordial Follicle Recruitment by Anti-Mullerian Hormone in the Mouse Ovary", Endocrinology 140, 5789-5796 (1999).
Gruijters, et al, "Anti-Mullerian hormone and its role in ovarian function", Molecular and Cellular Endocrinology 211, 85-90 (2003).
Hudson, et al, "An immunoassay to detect human Mullerian inhibiting substance in males and females during normal development", Journal of Clinical Endocrinology and Metabolism 70, 16-22 (1990).
Lee, et al, "Mullerian-inhibiting substance: A gonadal hormone with multiple functions", Endocrine Reviews 14(2), 152-164 (1993).
Lee, et al, "Mullerian Inhibiting Substance in human: normal levels from infancy to adulthood", Journal of Clinical Endocrinology and Metabolism 81, 571-575 (1996).
Lee, et al, "MIS/AMH in the assessment of cryptochidism and intersex conditions", Molecular and Cellular Endocrinology 211, 91-98 (2003).
Long, et al, "Detection of minimal levels of serum anti-Mullerian hormone during follow-up of patients with ovarian granulosa cell tumor by means of a highly sensitive enzyme-linked immunosorbent assay", Journal of Clinical Endocrinology Metabolism 85, 540-544 (2000).
Picard, et al., "Cloning and expression of cDNA for anti-Mullerian hormone", Proc Natl Acad Sci 83, 5464-5468 (1986).
te Velde, et al., "The variability of female reproductive ageing", Human Reproduction. Update 8, 141-154 (2002).
Teixeira, et al, "Mullerian Inhibiting Substance: An Instructive Developmental Hormone with Diagnostic and Possible Therapeutic Applications", Endocrine Reviews 22, 657-674 (2001).
van Rooij, et al, "Serum anti-Mullerian hormone levels: a novel measure of ovarian reserve", Human Reproduction 17, 3065-3071 (2002).
Wilson, et al, "Mullerian inhibiting substance requires its N-terminal domain for maintenance of biological-activity, a novel finding within the transforming growth-factor beta superfamily", Molecular Endocrinology 7, 247-257 (1993).
Belville, et al, "Mutations of the Anti-Mullerian Hormone Gene in Patients with Persistent Mullerian Duct Syndrome: Biosynthesis, Secretion, and Processing of the Abnormal Proteins and Analysis Using a Three-Dimensional Model", Molecular Endocrinology 18(3): 708-721 (2004).
MacLaughlin, et al, "Mullerian Duct Regression and Antiproliferative Bioactivities of Mullerian Inhibiting Substance Reside in its Carboxy-Terminal Domain", Endocrinology 131(1):291-296 (1992).
Necklaws, et al, "Detection of Mullerian Inhibiting Substance in Biological Samples by a Solid Phase Sandwich Radioimmunoassay", Endocrinology 118(2): 791-796 (1986).

OTHER PUBLICATIONS

Shima et al., "Production of Monoclonal Antibodies for Affinity Purification of Bovine Mullerian Inhibiting Substance Activity", *Hybridoma*, vol. 3, No. 3, 1984, pp. 201-214.

*Primary Examiner* — Elizabeth C. Kemmerer
(74) *Attorney, Agent, or Firm* — Merchant & Gould P.C.

(57) ABSTRACT

The present invention discloses compositions and methods to measure an amount of Anti-Mullerian Hormone (AMH) in a sample, including a mammalian sample such as a primate, rodent, equine, or bovine sample. The compositions and methods herein also provide antibodies that bind to epitopes on AMH that are stable to proteolysis of AMH.

18 Claims, 6 Drawing Sheets

IMMUNOLOGICAL ASSAY AND ANTIBODIES FOR ANTI-MULLERIAN HORMONE

BACKGROUND OF THE INVENTION

1. Field of the Invention

The present invention relates generally to immunological assays and methods to measure biological compounds. More specifically, the present invention relates to novel methods of measuring Anti-Müllerian Hormone (AMH) in a sample, including a mammalian sample such as a human, mouse or rat sample. In particular, antibodies are provided that bind to the mature region of Anti-Mullerian Hormone.

2. Description of the Related Art

Anti-Müllerian Hormone (AMH), also known as Müllerian-Inhibiting Substance (MIS), is a 140-kilodalton (kDa) dimeric glycoprotein hormone belonging to the transforming growth factor β (TGF β) superfamily, which includes TGF-β and the various inhibin and activin glycoproteins (Teixeira et al., 2001). All members of this superfamily are dimeric glycoproteins, and all are involved in the regulation of tissue growth and differentiation. In common with other TGF-β proteins, AMH is synthesized as a large precursor with a short signal sequence followed by the pre-pro hormone that forms homodimers. Prior to secretion, the mature hormone undergoes glycosylation and dimerisation to produce a 140-kDa dimer of identical disulphide-linked 70-kDa monomer subunits; each monomer contains an N-terminal domain (also called the "pro" region) and a C-terminal domain (also called the "mature" region). In contrast to other TGF-β superfamily members, it is believed that AMH requires the N-terminal domain to potentiate activity of the C-terminal domain to attain full bioactivity (Wilson et al., 1993). Between 5-20% of AMH is then cleaved at a specific site between the N-terminal domain (the pro region) and the C-terminal domain (the mature region) of the 70-kDa monomer during cytoplasmic transit, to form two polypeptides of 58 kDa (pro region) and 12 kDa (mature region). These two parts of the monomer remain in non-covalent attachment. The human gene coding for AMH has been sequenced and isolated, and is located on the short arm of chromosome 19 (Picard et al., 1986). The structure of a specific receptor for AMH has also been isolated and characterized (di Clemente et al., 1994; Barrends et al., 1995). Across species, AMH retains 11 to 12 conserved cystine residues, of which seven are located in the mature region. This region demonstrates the greatest degree of amino acid sequence homology between species, with 108 of the last 112 residues being conserved between the rat and human sequences (Lee et al., 1993).

AMH has an important role in sexual differentiation during development. AMH is produced by the Sertoli cells of the testis in the male, and by ovarian granulosa cells in the female. During fetal development in males, secretion of AMH from testicular Sertoli cells is essential for the regression of the Mullerian ducts, and thus the normal development of the male reproductive tract (Picon et al., 1969). The Mullerian ducts are the primordium for the uterus, Fallopian tubes, and upper part of the vagina in the female. In the male, secretion of AMH by the Sertoli cells commences during embryogenesis and continues throughout life. Levels drop following puberty, decreasing slowly to a relatively low post-puberty value (Teixeira et al., 2001). In the female, serum AMH is maintained at relatively low levels when compared to the male. After puberty, when menstrual cycling begins, circulating AMH slowly decreases throughout life and becomes undetectable at menopause. In mice, ablation of AMH function causes increased loss of ovarian follicles and premature cessation of ovarian cycling (Durlinger et al., 1999).

Several clinical applications for measuring serum AMH in humans have been identified. Among these are the diagnosis of intersex disorders in children (Lee et al., 2003), precocious puberty and the delayed onset of puberty, cryptorchidism, anorchidism, and evaluation of male gonadal function (Teixeira et al., 2001). Other potential applications include the investigation of the peri-menopausal transition in women, and the detection and monitoring of granulosa cell cancer patients (Long et al., 2000). Recent work has shown AMH to have potential as a circulating marker for assessment of ovarian reserve and fertility in women (van Rooij et al., 2002; te Velde et al., 2002; Gruijters et al., 2003). After many years in which AMH could be described as an esoteric analyte, there is now considerable interest in its potential as a routine clinical marker.

Almost all previous AMH research studies have been carried out with one of two immunoassays. One assay developed by Hudson et al. (Hudson et al., 1990) uses two monoclonal antibodies raised against human recombinant AMH, both being directed to epitopes in the pro region of the molecule. Use of this assay to measure AMH in humans from infancy to adulthood has been reported by Lee et al. (1996). Lee et al. (1996) also report that AMH is stable when stored at −20° C. for up to 2 years or for up to three freeze-thaw cycles, but that measured values increased by 2- to 3-fold beyond 2 years of storage, and decreased by 50% or more after three freeze-thaw cycles. In addition, Lee et al. (1996) report that the antibodies used in the Hudson assay do not recognize the carboxy-terminal fragment (mature region) of AMH, and while they are highly specific for full-length unprocessed human AMH (unprocessed meaning not being cleaved between the pro and mature regions of the 70-kDa monomer), they have a much lower affinity for the amino-terminal fragment (pro region) than for the unprocessed protein. Accordingly, some of the individual variability in AMH concentrations reported by Lee et al. (1996) may be due to differences in the extent of processing of the AMH protein that occurs in vivo. Lee et al. (1996) also report that the Hudson assay antibodies recognize non-human primate as well as human AMH, but that they do not recognize bovine or rodent AMH. A second assay employed in AMH research studies uses a pair of monoclonal antibodies, one of which is to an epitope in the pro region and the other is to an epitope in the mature region of human AMH (Long et al., 2000). A third more recently described assay uses two monoclonal antibodies against the pro region (Al-Qahtani et al., 2005).

Proteolysis of AMH in samples measured using currently available assays has also been reported, so that particularly careful attention to sample collection and storage may be required if reliable results are to be obtained. The pro region of AMH is subject to proteolytic cleavage during incubation in solution (Cate et al., U.S. Pat. No. 5,359,033). The mature region of AMH is more stable against proteolysis compared to the pro region, in part because of its multiple cystine residues.

Previous AMH assays measure human AMH but cannot be used to measure AMH in rodent samples, probably because the amino acid sequence of the pro region varies considerably between species. The overall amino acid sequence homology between the pro regions in mouse, rat, human, bovine and chicken AMH varies from 37-89% (GenBank, National Centers for Biotechnology Information (NCBI) genetic database). Assays that can be used to measure AMH in multiple species, including mammalian species such as the mouse and rat as well as humans, have not previously been available in the art. In addition to clinical applications, such assays would have useful applications in research related to various clinical and other applications of AMH measurements. In addition, applications for the measurement of AMH would benefit from assays providing stable and accurate measured values of AMH in samples, including AMH measurements that are unaffected by proteolysis of AMH.

The present invention provides compositions and methods to measure AMH in a sample, and antibodies that bind to the mature region of AMH. The present invention also provides compositions and methods to measure AMH in biological samples, including mammalian samples such as human, monkey, mouse, rat, bovine and horse samples. In addition, the present invention provides compositions and methods to measure AMH in a sample, wherein the amount of AMH measured is not affected by proteolysis of AMH in the sample. Thus, the present invention fulfills these longstanding needs and desires in the art.

SUMMARY OF THE INVENTION

The present invention discloses compositions and methods to measure Anti-Mullerian Hormone (AMH) in a sample.

One embodiment of the present invention discloses a composition comprising a first antibody and a second antibody, wherein the first antibody binds to a first epitope and the second antibody binds to a second epitope in a mature region of an Anti-Mullerian Hormone.

An additional embodiment discloses a method for measuring an amount of an Anti-Mullerian Hormone in a sample containing Anti-Mullerian Hormone comprising: combining a sample containing Anti-Mullerian Hormone with a known amount of labeled Anti-Mullerian Hormone to create a spiked sample; binding the Anti-Mullerian Hormone and the labeled Anti-Mullerian Hormone in the spiked sample to an antibody, wherein the antibody binds to a mature region of the Anti-Mullerian Hormone to create a complex, and to a mature region of the labeled Anti-Mullerian Hormone to create a labeled complex; measuring an amount of the labeled complex; and calculating the amount of Anti-Mullerian Hormone in the sample.

Another embodiment discloses a method for measuring an amount of an Anti-Mullerian Hormone in a sample containing Anti-Mullerian Hormone comprising: binding a first antibody to an Anti-Mullerian Hormone, wherein the first antibody binds to a first epitope in a mature region of the Anti-Mullerian Hormone; binding a second antibody to the Anti-Mullerian Hormone, wherein the second antibody binds to a second epitope in the mature region of the Anti-Mullerian Hormone, thereby creating an amount of bound second antibody; measuring the amount of bound second antibody; and calculating the amount of Anti-Mullerian Hormone in the sample.

Yet another embodiment discloses a composition for measuring an amount of Anti-Mullerian Hormone in a sample comprising: a first antibody and a second antibody that bind to a mature region of an Anti-Mullerian Hormone, wherein the first antibody binds to a first epitope and the second antibody binds to a second epitope in the mature region of the Anti-Mullerian Hormone; a solid support coupled with the first antibody; and a label coupled with the second antibody.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1(A-B) show Western blots demonstrating that AMH antibody F2B7A (antibody 7A) binds to rat and human AMH under reduced and non-reduced conditions.

FIGS. 2(A-B) show Western blots demonstrating that AMH antibody F2B12H (antibody 12H) recognizes the mature region of both human and rat AMH under non-reduced conditions.

FIGS. 4(A-C) show Western blot assays of rat and human recombinant AMH probed with AMH antibodies 5/6, 2/6 and 9/6 as probes, where the human AMH (hAMH) was stored under various conditions. FIG. 4A shows that antibody 5/6 recognizes the mature region (12 kDa) of human recombinant and rat AMH. FIG. 4B shows that antibody 2/6 recognizes the pro region of human recombinant AMH, including both bands that are produced after proteolytic cleavage of the "additional cleavage site". The 2/6 antibody epitope is thus stable to the proteolysis, because the antibody recognizes both bands. Antibody 2/6 does not recognize rat AMH. FIG. 4C shows that antibody 9/6 recognizes the pro region of rat and human AMH, but does not recognize the smaller fragment after proteolytic cleavage of the pro region of human recombinant AMH at the "additional cleavage site". The 9/6 antibody epitope is thus not stable to the proteolysis.

FIGS. 6(A-B) show measurements of AMH serum levels during the estrous cycle in female mice, using the 12H and 7A antibodies in an immunoassay. FIG. 6(A) shows a bar graph of AMH measurements in the mouse in different stages in the estrous cycle. FIG. 6(B) shows a correlation graph of the number of small antral follicles in different states in the estrous cycle.

DETAILED DESCRIPTION OF THE INVENTION

The present invention is directed toward compositions and methods to measure Anti-Mullerian Hormone (AMH) in a sample.

The present invention discloses a composition comprising a first antibody and a second antibody, wherein the first antibody binds to a first epitope and the second antibody binds to a second epitope in a mature region of an Anti-Mullerian Hormone. Such antibodies are useful in immunoassays to measure an amount of AMH in a sample. The first and second antibodies may be monoclonal antibodies. Such antibodies may bind to epitopes in the mature region of AMH, or to epitopes that are partially located in the mature region of AMH and partially located in the pro region of AMH. The first epitope to which the first antibody binds may be different from the second epitope to which the second antibody binds, so that binding of one antibody to its epitope does not interfere with the binding of the other antibody. The first and second antibodies could also comprise antibody fragments.

In one aspect, a solid support may be bound to the first antibody. An antibody may be bound or coated on to such a solid support using techniques known in the art. Examples of a solid support, or alternatively a solid phase particle, include a protein binding surface, such as a microtiter plate, a colloidal metal particle, an iron oxide particle, a latex particle, a polymeric bead. Other examples of a solid support or solid phase particle include a paramagnetic bead, cellulose, agarose, dextran-coated charcoal, Ficoll, sephadex, glass beads, ceramic beads, or other inert surfaces known in the art suitable for protein binding.

In another aspect, a second antibody may coupled with a label, although alternatively both the first and the second antibody may be coupled with a different label. Such a label may be coupled with or conjugated with an antibody using techniques known in the art. Representative types of a label include a chemiluminescent agent, a colorimetric agent, an energy transfer agent, an enzyme, a fluorescent agent or a radioisotope. Such agents produce a detectable signal that is measured using methods known in the art; the measurements are then used to calculate the amount of an analyte in a sample using standard techniques. Examples of a chemiluminescent agent include an enzyme that produces a chemiluminescent signal in the presence of a substrate(s) that produce chemiluminescent energy when reacted with the enzyme. Examples of such an enzyme include horseradish peroxidase (HRP) and alkaline phosphatase (AP). Other examples of a chemiluminescent agent include a non-enzymatic direct chemiluminescent label, such as the Acridinium ester system. Examples of a calorimetric agent include an enzyme such as horseradish peroxidase, alkaline phosphatase, and acetylcholine esterase (AChE). One example of an energy transfer agent is fluorescent lanthanide chelates; fluorescent dyes may be used as fluorescent agents. Representative radioisotopes include 125I, 14C and 3H.

In another embodiment of the present invention, the compositions and methods disclosed herein are useful to measure an amount of Anti-Mullerian Hormone in a mammalian sample, which may include primate, rodent, equine, or bovine Anti-Mullerian Hormone. The primate Anti-Mullerian Hormone may include a human Anti-Mullerian Hormone, and the rodent Anti-Mullerian Hormone may include a mouse or a rat Anti-Mullerian Hormone. The sample containing the Anti-Mullerian Hormone to be measured may be a biological sample, such as cell lysates or culture medium, or a body fluid such as serum, plasma, cerebrospinal fluid, saliva, urine, milk, semen or other body fluid.

Another embodiment discloses a method for measuring an amount of an Anti-Mullerian Hormone in a sample containing Anti-Mullerian Hormone comprising: combining a sample containing Anti-Mullerian Hormone with a known amount of labeled Anti-Mullerian Hormone to create a spiked sample; binding the Anti-Mullerian Hormone and the labeled Anti-Mullerian Hormone in the spiked sample to an antibody, wherein the antibody binds to a mature region of the Anti-Mullerian Hormone to create a complex, and to a mature region of the labeled Anti-Mullerian Hormone to create a labeled complex; measuring an amount of the labeled complex; and calculating the amount of Anti-Mullerian Hormone in the sample. In one embodiment, such a method further comprises a solid support bound to the antibody, wherein the solid support may comprises a protein binding surface such as a microtiter plate, a colloidal metal particle, an iron oxide particle, a latex particle or a polymeric bead. The labeled Anti-Mullerian Hormone may comprise a label such as a chemiluminescent agent, a calorimetric agent, an energy transfer agent, an enzyme, a fluorescent agent, or a radioisotope.

The Anti-Mullerian Hormone measured may comprise a mammalian Anti-Mullerian Hormone including primate Anti-Mullerian Hormone such as human Anti-Mullerian Hormone, rodent Anti-Mullerian Hormone such as rat or mouse Anti-Mullerian Hormone, equine, and bovine Anti-Mullerian Hormone.

Embodiments as described herein may be used in various types of immunoassays, which may include a competitive type of immunoassay. Examples of immunoassays that may be competitive include an enzyme immunoassay or enzyme-linked immunosorbent assay (EIA or ELISA), a fluorescent immunoassay, a radiometric or radioimmunoassay (RIA), a magnetic separation assay (MSA), a lateral flow assay, a diffusion immunoassay, an immunoprecipitation assay, an immunosorbent or "antigen-down" assay using an analyte bound to a solid support, or a an agglutination assay. In one such assay, a sample contains an unknown amount of analyte to be measured, which may be a protein such as Anti-Mullerian Hormone. The analyte may also be termed an antigen. The sample may be spiked with a known or fixed amount of labeled analyte. The spiked sample is then incubated with an antibody that binds to the analyte, so that the analyte in the sample and the labeled analyte added to the sample compete for binding to the available antibody binding sites. More or less of the labeled analyte will be able to bind to the antibody binding sites, depending on the relative concentration of the unlabeled analyte present in the sample. Accordingly, when the amount of labeled analyte bound to the antibody is measured, it is inversely proportional to the amount of unlabeled analyte in the sample. The amount of analyte in the original sample may then be calculated based on the amount of labeled analyte measured, using standard techniques in the art.

In another type of competitive immunoassay, an antibody that binds to the analyte may be coupled with or conjugated with a ligand, wherein the ligand binds to an additional antibody added to the sample. One example of such a ligand includes fluorescein. The additional antibody may be bound to a solid support. The additional antibody binds to the ligand coupled with the antibody that binds in turn to the analyte or alternatively to the labeled analyte, forming a mass complex which allows isolation and measurement of the signal generated by the label coupled with the labeled analyte. In another type of competitive immunoassay, the analyte to be measured may be bound to a solid support, and incubated with both an antibody that binds to the analyte and a sample containing the analyte to be measured. The antibody binds to either the analyte bound to the solid support or to the analyte in the sample, in relative proportions depending on the concentration of the analyte in the sample. The antibody that binds to the analyte bound to the solid support is then bound to another antibody, such as anti-mouse IgG, that is coupled with a label. The amount of signal generated from the label is then detected to measure the amount of antibody that bound to the analyte bound to the solid support. Such a measurement will be inversely proportional to the amount of analyte present in the sample. Such an assay may be used in a microtiter plate format. Another immunoassay that may be competitive includes an agglutination assay. In such an assay, the analyte to be measured in the sample competes with analyte that is bound to a first solid support particle, such as Ficoll, for the binding sites of an anti-analyte antibody. The antibody may be bound to or coated on a second solid support particle. Cross-binding or agglutination between the particles occurs as the analyte molecules bound to the first solid support particles bind to the antibody molecules bound to the second solid support particles, to form clumps of co-agglutination lattice. Alternatively, the antibody molecules bind to the free analyte in the sample, so that the amount of agglutination is inversely proportional to the amount of analyte in the sample. The amount of agglutination may be measured using standard techniques, such as spectrophotometry.

An additional embodiment of the present invention discloses a method for measuring an amount of an Anti-Mullerian Hormone in a sample containing Anti-Mullerian Hormone comprising: binding a first antibody to an Anti-Mullerian Hormone, wherein the first antibody binds to a first epitope in a mature region of the Anti-Mullerian Hormone; binding a second antibody to the Anti-Mullerian Hormone, wherein the second antibody binds to a second epitope in the mature region of the Anti-Mullerian Hormone, thereby creating an amount of bound second antibody; measuring the amount of bound second antibody; and calculating the amount of Anti-Mullerian Hormone in the sample. In one aspect, a solid support may be bound to the first antibody. The solid support may comprise a protein binding surface, such as a microtiter plate, a colloidal metal particle, an iron oxide particle, a latex particle or a polymeric bead. In another aspect, a label may be coupled with the second antibody. Possible labels include a chemiluminescent agent, a colorimetric agent, an energy transfer agent, an enzyme, a fluorescent agent or a radioisotope.

Embodiments of the invention as disclosed herein may be used to perform immunoassays referred to as immunometric, "two-site" or "sandwich" immunoassays, wherein the analyte may be bound to or sandwiched between two antibodies that bind to different epitopes on the analyte. Representative examples of such immunoassays include enzyme immunoassays or enzyme-linked immunosorbent assays (EIA or ELISA), immunoradiometric assays (IRMA), fluorescent immunoassays, lateral flow assays, diffusion immunoassays, immunoprecipitation assays, and magnetic separation assays (MSA). In one such assay, a first antibody, which may be described as the "capture" antibody, may be bound to a solid support, such as a protein binding surface, colloidal metal particles, iron oxide particles, latex particles or polymeric beads. The capture antibody may be bound to or coated on a solid support using procedures known in the art. Alternatively, the capture antibody may be coupled with a ligand that is recognized by an additional antibody that is bound to or coated on a solid support. Binding of the capture antibody to the additional antibody via the ligand then indirectly immobilizes the capture antibody on the solid support. An example of such a ligand is fluorescein. The second antibody, which may be described as the "detection" antibody, may be coupled with a label, which may comprise a chemiluminescent agent, a calorimetric agent, an energy transfer agent, an enzyme, a fluorescent agent or a radioisotope. The detection antibody may be coupled with or conjugated with a label using procedures known in the art. The label may comprise a first protein such as biotin coupled with the second antibody, and a second protein such as streptavidin that is coupled an enzyme. The second protein binds to the first protein. The enzyme produces a detectable signal when provided with substrate(s), so that the amount of signal measured corresponds to the amount of second antibody that is bound to the analyte. Horseradish peroxidase is an example of such an enzyme; possible substrates include TMB (3,3', 5,5'-tetramethyl benzidine, OPD (o-phenylene diamine), and ABTS (2,2'-azino-bis(3-ethyl-benzthiazoline-6-sulfonic acid).

An additional embodiment of the present invention discloses a composition for measuring an amount of Anti-Mullerian Hormone in a sample comprising: a first antibody and a second antibody that bind to a mature region of an Anti-Mullerian Hormone, wherein the first antibody binds to a first epitope and the second antibody binds to a second epitope in the mature region of the Anti-Mullerian Hormone; a solid support coupled with the first antibody; and a label coupled with the second antibody. The Anti-Mullerian Hormone measured may comprise a mammalian Anti-Mullerian Hormone, including primate, rodent, equine, and bovine Anti-Mullerian Hormone. Such compositions may be used to measure human, rat or mouse Anti-Mullerian Hormone, as well as Anti-Mullerian Hormone of other species including horse, bull and monkey Anti-Mullerian Hormone. In one aspect, the solid support comprises a protein binding surface, which may include a microtiter plate, a colloidal metal particle, an iron oxide particle, a latex particle or a polymeric bead. The label may comprise a chemiluminescent agent, a calorimetric agent, an energy transfer agent, an enzyme, a fluorescent agent or a radioisotope, or another type of label known in the art. Such compositions as disclosed in the present invention may comprise kits useful for measuring Anti-Mullerian Hormone in a sample.

Another possible embodiment of the present invention discloses antibodies that bind to epitopes in a mature region of Anti-Mullerian Hormone, where the epitopes are stable to proteolysis. As a result, the amount of the Anti-Mullerian Hormone measured in a sample is not affected by proteolysis of the Anti-Mullerian Hormone in the sample. Because the antibody epitopes are not destroyed by proteolysis, it is thereby possible to accurately measure Anti-Mullerian Hormone in samples using assay conditions standard in the art, including extended incubation times.

The following examples are given for the purpose of illustrating various embodiments of the invention and are not meant to limit the present invention in any fashion:

Example 1

Antibody Production

Female AMH null mice on a C57B1/6J background were immunized with recombinant human AMH prepared as described previously (Hudson et al., 1990). An initial injection of 50 µg of recombinant human AMH was given subcutaneously in Ribi adjuvant (Sigma M6536) and two similar booster injections were given to each animal at 4-week intervals. Four days after the third boost, 5 µl of blood was taken from each animal for screening by ELISA. Each sample was diluted in 2 ml of PBS containing 1% BSA (w/v) and 0.1% (w/v) $NaN_3$ as a preservative and screened as follows: Nunc Maxisorb plates (SLS, UK) were coated with recombinant human AMH supplied by Dr Richard Cate (Biogen, Cambridge, Mass. USA) at 0.1 µg/ml in 0.2M sodium carbonate-bicarbonate buffer, pH 9.4 (Perbio) overnight (50 µl/well). Following adsorption, the plates aspirated and blocked with 100 µl per well of 1% (w/v) BSA in PBS for an hour. The plates were then washed with wash buffer (0.05M Tris-HCl buffer containing 0.15M NaCl and 0.05% (v/v) Tween-20 (Sigma)) before the sera of the animals was titrated across the plates diluted in Tris conjugate buffer (1% BSA (w/v) in 25 mM Tris-HCl, pH 7.5 containing 0.15M NaCl and 0.5% (w/v) Tween 20) and incubated at room temperature for an hour. The plates were then thoroughly washed with wash buffer and 50 µl of a 1:2000 dilution of horse radish peroxidase conjugated goat anti-mouse IgG (HRP, Dako) in Tris conjugate buffer added to each well. After incubation period of 30 minutes the plates were washed and 50 µl/well of TMB (tetramethylbenzidine peroxidase (Dynatech)) added. When a suitable level of colour was reached (approx. 10-15 minutes), the reaction was stopped by the addition of 50 μl of 6% (v/v) ortho-phosphoric acid (BDH) to each well. Absorbance at 450 nm was measured using a Biotek plate reader (Bio-Tek instruments). The highest responding animal was selected and processed for spleen hyper stimulation prior to sacrifice. Final boosting was carried out by injecting 50 μg of sterile AMH intravenously. The spleen was removed aseptically, aliquoted and stored in liquid nitrogen prior to fusion.

Example 2

Antibody screening. One aliquot of splenocytes was fused with SP2/0 myeloma cells in the presence of polyethylene glycol (Boehringer Mannheim), according to Köhler and Milstein (Lee et al., 1996). Fusions were screened first by ELISA on AMH which is an *E. coli* expressed version of only the human mature region (R & D Systems). A second round of screening was performed on ELISA plates coated with a preparation of intact rat AMH, as described by Weenen et al. (Weenen et al, Mol Hum Reprod 2004). High responding clones were recloned on methylcellulose medium (Clonacell HY) and cell lines were grown up in growth medium containing low concentrations of IgG. Antibodies were purified by protein G chromatography and biotinylated with water soluble LC biotin ester (Pierce Chemicals). Procedures used were from standard protocols (Harlow and Lane). These clones selected for immunoassay studies were thus screened to provide epitopes in AMH that are at least partially in the mature region of AMH, and that are common to rat and human AMH. The following clones were selected for further analysis: F2/A4, F2/A2, F2B/12F, F2B/7H, F2B/7A, F2B/12H, F2B/6L, F2B/7C, F2B/5B, and F2A/23.

Example 3

Western Blotting. Western blot analysis was performed using the mouse monoclonal antibodies 5/6A, 9/6, 2/6, F2B12H (antibody 12H) and F2B7A (antibody 7A). The 5/6A, 9/6, and 2/6 antibodies are antibodies to human AMH described previously (Al-Qahtani et al., 2005); results obtained using these antibodies are shown here for the purpose of comparison to the characteristics of the 12H and 7A antibodies. The 5/6A antibody binds to the mature region of human AMH; the 2/6 and 9/6 antibodies bind to the pro region of human AMH. Recombinant rat and human AMH were separated using 10% polyacrylamide gel electrophoresis under reducing or non-reducing conditions. Proteins were transferred to nitrocellulose membranes and incubated with the antibody at a 1:1000 dilution, followed by a secondary peroxidase-conjugated goat anti-mouse antibody at a 1:10000 dilution. Proteins were visualized by the ECL plus Western blotting detection system (Amersham Biosciences).

Figure 1A:
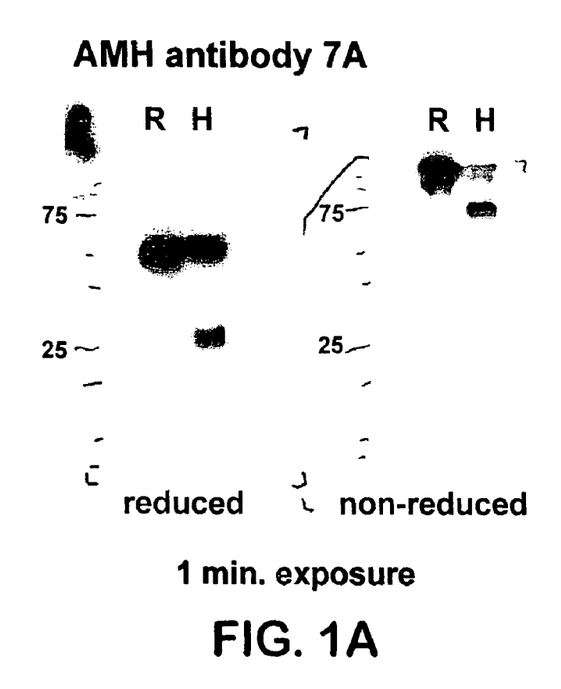
Figure 1B:
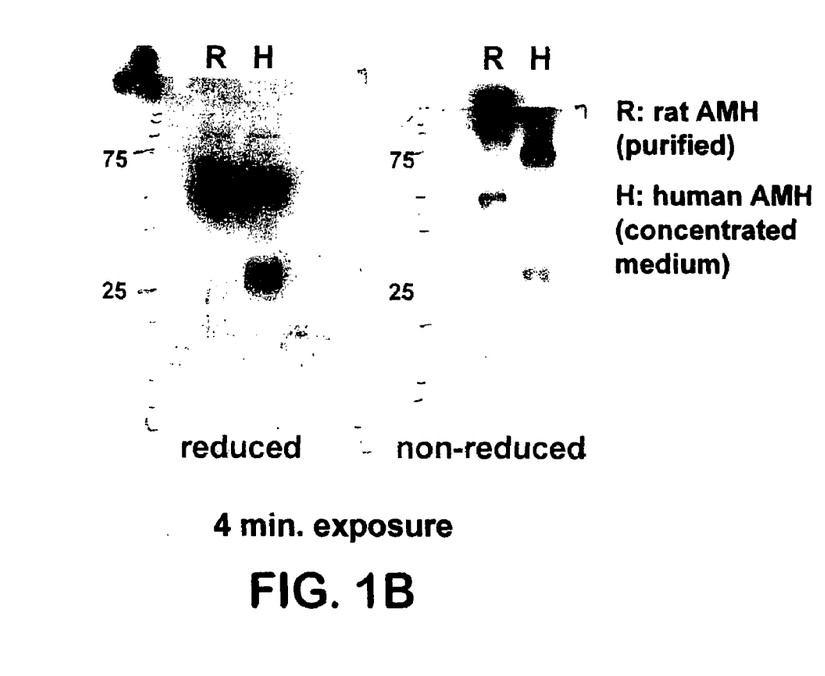
Figure 3:
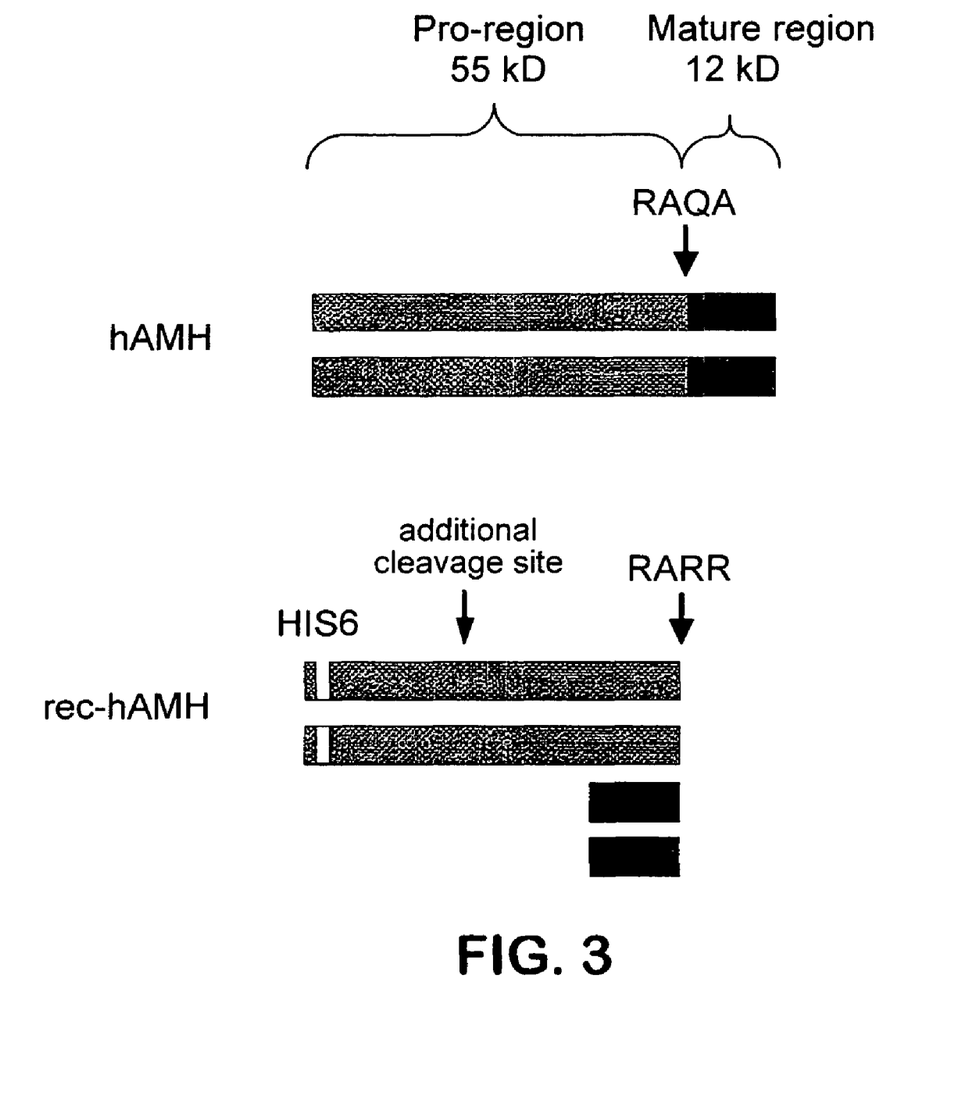
FIG. 3 shows the proteolytic processing of recombinant human AMH into the pro and mature regions. The "additional cleavage site" is also shown that exists within the pro-region of recombinant human AMH.

FIGS. 1(A-B) show Western blots demonstrating that AMH antibody F2B7A (antibody 7A) binds to rat and human AMH under reduced and non-reduced conditions. The 1-minute exposure in FIG. 1A shows that antibody 7A (AB 7A) recognizes the pro-region of rat and recombinant human AMH, both under reduced and non-reduced conditions (58-kD band). An additional band (about 25 kDa) is seen after cleavage of the "additional cleavage site" that exists within the pro region of human AMH, under reduced and non-reduced conditions (see lanes "H" and FIG. 3). The 4-minute exposure of the same blot in FIG. 1B shows that after longer exposure, antibody 7A recognizes the mature region of both rat and recombinant human AMH under non-reduced conditions (12-kDa band).

Figure 2A:
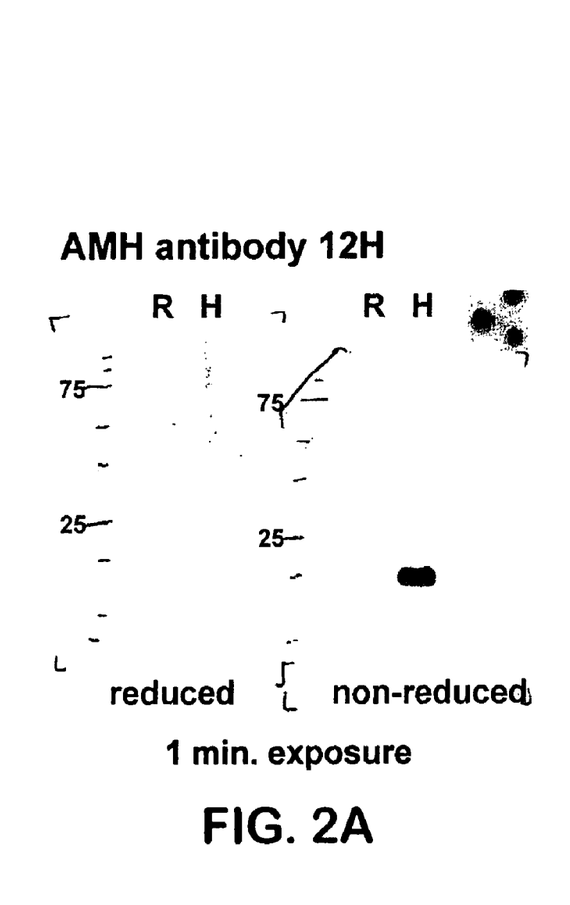
Figure 2B:
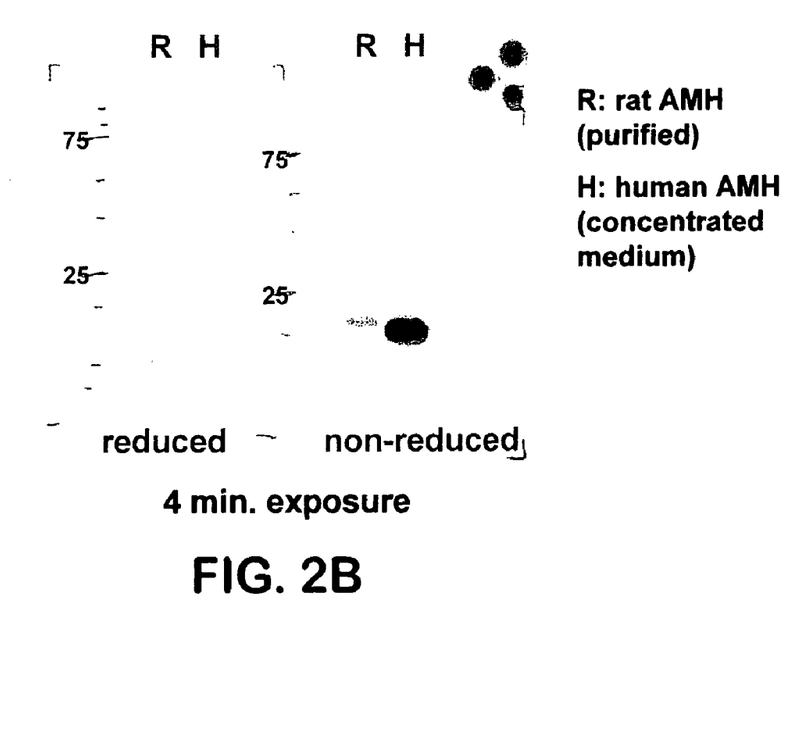

FIGS. 2(A-B) show Western blots demonstrating that AMH antibody F2B12H (antibody 12H) recognizes the mature region of both human and rat AMH under non-reduced conditions. FIG. 2A shows that antibody 12H recognizes the mature region of recombinant human and rat AMH under non-reduced conditions but not reduced conditions, on 1-minute exposure (12-kDa bands). FIG. 2B shows on a 4-minute exposure of the same blot that antibody 12H also recognizes the pro-regions of both recombinant human and rat AMH, under non-reduced but not reduced conditions (58-kDa bands).

Example 4

Coating of Plates for Mouse Immunoassay Work

The following protocol was used to provide coated plates for immunoassay testing of candidate antibodies for measuring AMH in mouse samples:

1. Nunc maxisorb plates were coated with 0.05 ml each of the antibodies at a concentration of 2 micrograms per ml in 0.05M bicarbonate buffer pH 9.4.

2. Plates were left to coat overnight.

3. Plates were aspirated individually, banged dry on towelling and 200 microliters of 0.5% (w/v) casein buffer containing 6% sucrose was added. The casein buffer (CLB-M2052) was obtained from the Mast Cell Group, Derby Road, Bootle, Merseyside, L20 1EA, UK The casein buffer is supplied as a 5% solution and is diluted ten fold in PBS before use.

4. After 1 hour to allow the casein to block the excess sites on the plastic the contents of the wells were banged out completely on paper towel and the plate places in a drying chamber with forced air flow from an industrial humidifier (Munters).

5. After drying overnight each plate was sealed in an aluminium pouch containing a dessicant bag.

Example 5

Selection of Pairs of Antibodies for Immunoassay

The following standard assay protocol was adopted for testing various pairs of antibodies for their ability to measure AMH by two-site ELISA. All plate washing was done with PBS containing 0.05% (w/v) tween 20.

1. Standards and samples were diluted in HPE commercial assay diluent (CLB M1940) obtained from the Mast cell group. This is provided as a 5× concentrate to be diluted in water to give working strength.

2. 0.05 ml of each sample or standard were added in duplicate to well on the plate.

3. The plate was covered and incubated for 2 hours on a shaker.

4. The plate was washed (5×) and an appropriate biotinylated antibody added at a final concentration of 0.3 micrograms/ml in working strength casein buffer. 0.05 ml of the biotinylated antibody was added to each well and the plate shaken for 1 hour at room temperature.

5. The plate was washed and a 1 in 10,000 dilution of poly HRP streptavidin conjugate added. The stock conjugate was obtained from the Mast Group as CLB M2051. It is stored at minus 20 centigrade until use. The dilution of the conjugate is made in working strength casein buffer.

6. The plate was incubated on the shaker for 30 min and then washed and banged dry and 0.1 ml of KPL peroxidase substrate added.

7. Colour development processed and the plate is stopped after 10-20 min by addition of 0.1 ml of 6% phosphoric acid.

8. Absorbance was read at 450 nm against a 620 nm blank

Example 6

Antibody Immunoassay. Pairs of antibodies generated as described herein were tested in an ELISA procedure to determine their ability to detect AMH in samples from several species. The results of immunoassays using such antibody pairs was compared to results of similar immunoassays using previously developed antibodies against AMH, described previously (Al-Qahtani et al., 2005). The results are shown in Table 1.

TABLE 1

Immunoassay results of six different combinations of capture and detector antibody.

| Sample number | Sample | F2B/7A plate F2A/4 label Ng/ml AMH from human standard | F2B/7A plate F2A2 label Ng/ml AMH from human standard | F2B/12H plate F2B/7A label Ng/ml AMH from Human standard | F2A2 plate F2B/7A label Ng/ml AMH from human standard | F2B12/F plate F2B/7A label Ng/ml AMH from human standard | F2B/7H Plate F2B/7A label Ng/ml AMH from human standard | F2A/4 plate F2B/7A label Ng/ml AMH from human standard | Values Obtained using the existing Brookes assay with 9/6 label and 2/6 detection |
|---|---|---|---|---|---|---|---|---|---|
| 1 | Steer serum 66 | UD | UD | UD | UD | UD | UD | UD | |
| 2 | Bull serum 67 | 1.46 | 0.96 | 0.7 | 0.9 | 0.4 | 0.6 | 2.1 | |
| 3 | Ovx cow serum 68 | .41 | 0.3 | UD | 0.3 | UD | 0.3 | 0.4 | |
| 4 | Sow 28. 1.1 year old | UD | UD | UD | UD | UD | UD | UD | |
| 5 | Sow 37 2.4 year old | UD | UD | UD | UD | UD | UD | UD | |
| 6 | Horse serum | .51 | 0.3 | 0.4 | 0.37 | UD | 0.5 | 0.3 | |
| 7 | Mouse serum A | UD | 1.39 | 2.4 | 1.3 | 2.7 | 2.7 | UD | |
| 8 | Mouse serum B | UD | 6.8 | 8.8 | 6.8 | 6.1 | 9.4 | 0.3 | |
| 9 | Donkey serum | UD | UD | UD | UD | UD | UD | UD | |
| 10 | Rabbit serum | UD | UD | UD | UD | UD | UD | UD | |
| 11 | Goat serum | UD | UD | UD | UD | UD | 0.3 | UD | |
| 12 | Heifer 12 months | UD | UD | UD | UD | UD | 0.3 | 0.3 | |
| 13 | Cow 8 years old | UD | UD | UD | UD | UD | 0.3 | 0.3 | |
| 14 | Cow 12 years old | UD | UD | UD | UD | UD | UD | 0.4 | |
| 19 | 2.5 ng/ml rat standard | 2.08 | 1.17 | 0.6 | 1.1 | 0.79 | 1.1 | 1.3 | |
| 25 | Human female serum 137 | 7.9 | 5.5 | 7.3 | 5.5 | 4.4 | 7.8 | 6.7 | 5.08 |
| 26 | Human female serum 216 | 3.47 | 2.0 | 3.3 | 2.0 | 2.3 | 3.6 | 2.8 | 1.37 |
| 27 | Human female serum 029 | UD | UD | UD | UD | UD | UD | UD | UD |
| 28 | Human female serum 081 | 5.1 | 3.4 | 4.8 | 3.4 | 3.2 | 5.3 | 4.7 | 2.16 |
| 29 | Human female serum 200 | 1.7 | 1.1 | 1.5 | 1.1 | 1.4 | 1.7 | 1.5 | 1.05 |
| Estimated detection limit for human in assay diluent | | 0.039 ng/ml | 0.3 ng/ml | 0.013 ng/ml | 0.013 ng/ml | 0.078 ng/ml | 0.078 ng/ml | 0.026 | |

TABLE 1-continued

Immunoassay results of six different combinations of capture and detector antibody.

| Sample number | Sample | F2B/7A plate F2A/4 label Ng/ml AMH from human standard | F2B/7A plate F2A2 label Ng/ml AMH from human standard | F2B/12H plate F2B/7A label Ng/ml from Human standard | F2A2 plate F2B/7A label Ng/ml from human standard | F2B12/F plate F2B/7A label Ng/ml from human standard | F2B/7H Plate F2B/7A label Ng/ml from human standard | F2A/4 plate F2B/7A Ng/ml from human standard | Values Obtained using the existing Brookes assay with 9/6 label and 2/6 detection |
|---|---|---|---|---|---|---|---|---|---|
| Estimated Rat cross reaction | | 83% | 46% | 24% | 44% | 31% | 44% | 52% | |
| | | | | Best cross reaction for mouse AMH | | | | | |

In Table 1 above, "plate" denotes the capture antibody bound to a plate surface, and "label" denotes the detection antibody coupled with a label; "UD" denotes "undetectable." The column on the far right of Table 1 shows results obtained using antibodies 9/6 and 2/6 against AMH (the "existing Brookes assay") that were previously developed (Al-Qahtani et al., 2005). The 9/6 and 2/6 antibodies both bind to the pro region of AMH. The results in Table I show that use of the F2B/12H (antibody 12H) and F2B/7A (antibody 7A) antibodies are effective in an assay to measure AMH in human, rat and mouse samples. Using the F2B/12H antibody for capture and the F2B/7A antibody for detection provides the highest estimate of AMH in the mouse sera, a sensitive assay for human AMH, and good cross reaction (24%) with recombinant rat AMH. Good correlation is observed with values obtained with the assay using the 9/6 and 2/6 antibodies, but with values approximately twice those obtained using the 9/6 and 2/6 antibodies.

Example 7

Stability of Recombinant Human AMH Immunoreactivity in Immunoassays

Figure 4A:
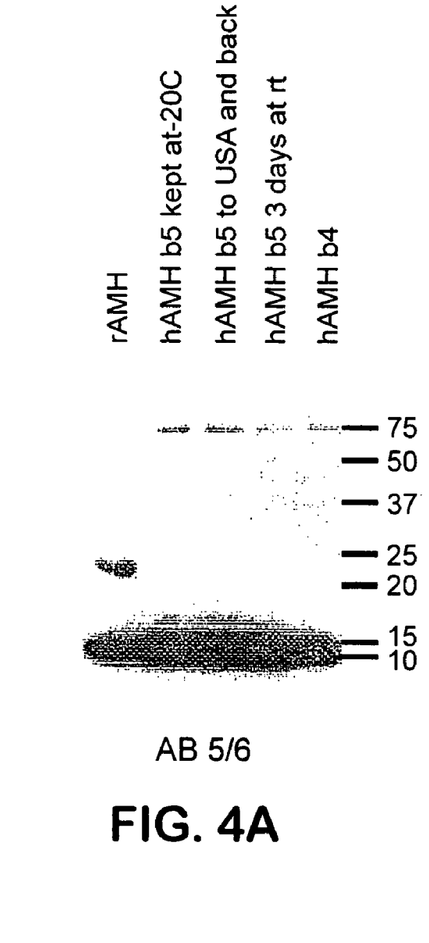
Figure 4B:
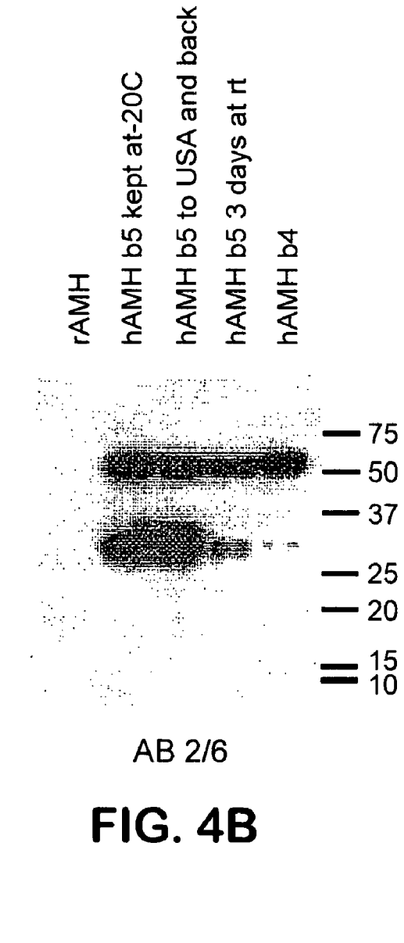
Figure 4C:
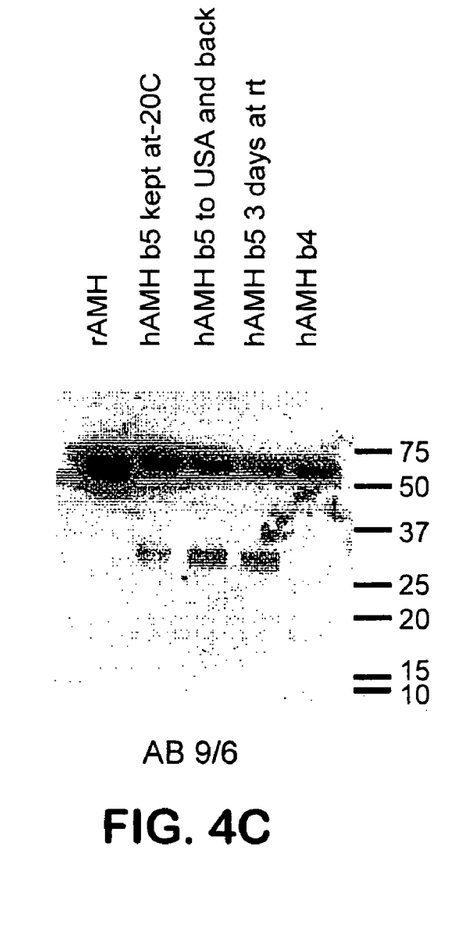

FIGS. 4(A-C) show Western blot assays of rat and human recombinant AMH probed with AMH antibodies 5/6, 2/6 and 9/6 as probes, where the human AMH (hAMH) was stored under various conditions. FIG. 4A shows that antibody 5/6 recognizes the mature region (12 kDa) of human recombinant and rat AMH. FIG. 4B shows that antibody 2/6 recognizes the pro region of human recombinant AMH, including both bands that are produced after proteolytic cleavage of the "additional cleavage site" (see FIG. 3). The 2/6 antibody epitope is thus stable to the proteolysis, because the antibody recognizes both bands. Antibody 2/6 does not recognize rat AMH. FIG. 4C shows that antibody 9/6 recognizes the pro region of rat and human AMH, but does not recognize the smaller fragment after proteolytic cleavage of the pro region of human recombinant AMH at the "additional cleavage site". The 9/6 antibody epitope is thus not stable to the proteolysis.

Table 2 shows the stability of human recombinant AMH immunoreactivity in ELISA immunoassays using the F2B/7A and F2B/12H antibodies, as compared to similar assays using the previously described 2/6 and 9/6 antibodies (Al-Qahtani et al., 2005).

TABLE 2

STABILITY OF AMH IMMUNOREACTIVITY

| | A Value obtained by immunoassay with 2/6 antibody for capture and 9/6 for detection. Read against Biogen standard | B Value obtained by immunoassay with F2B/12H antibody for capture and F2B/7A for detection. Read against Biogen standard | Comment |
|---|---|---|---|
| Solution of purified recombinant human AMH provided by Dr Axel Themmen of nominal concentration 30 micrograms/ml | 2.5 micrograms/ml | 29.4 micrograms/ml | A large part of the immunoreactivity in the 9/6 and 2/6 AMH assay has been lost from the Themmen recombinant preparation. |
| Solution of above AMH incubated for 6 days at 37° C. | 0.1 micrograms/ml | 30.1 micrograms/ml | In the F2B/7A and F2B/12H assay Themmen and Biogen AMH have similar immuno-reactivities and immuno-reactivity is stable to incubation at 37° C. |

In the initial immunoassay with the 2/6 and 9/6 antibody pair, recombinant human AMH preparations (obtained from Dr. Axel Themmen) were found to give concentration estimates that were very low compared to the Biogen human recombinant AMH. Subsequent work has shown that both of the epitopes for these antibodies are unstable to enzymes remaining in purified AMH. When the same recombinant human AMH preparation is incubated for 6 days at 37° C., the amount of apparent immunoreactivity decreases further. By contrast, the same recombinant human AMH preparation can be incubated for 6 days at 37° C. with insignificant reduction in immunoreactivity when measured using the F2B/12 and F2B/7A antibodies. This result requires both epitopes to be more stable to proteolysis than those recognised by the 9/6 and 2/6 antibodies. The incubated samples had 0.1% (w/v)

sodium azide added as a preservative. The Biogen recombinant human AMH was a gift of Dr Richard Cate.

Example 8

Figure 5:
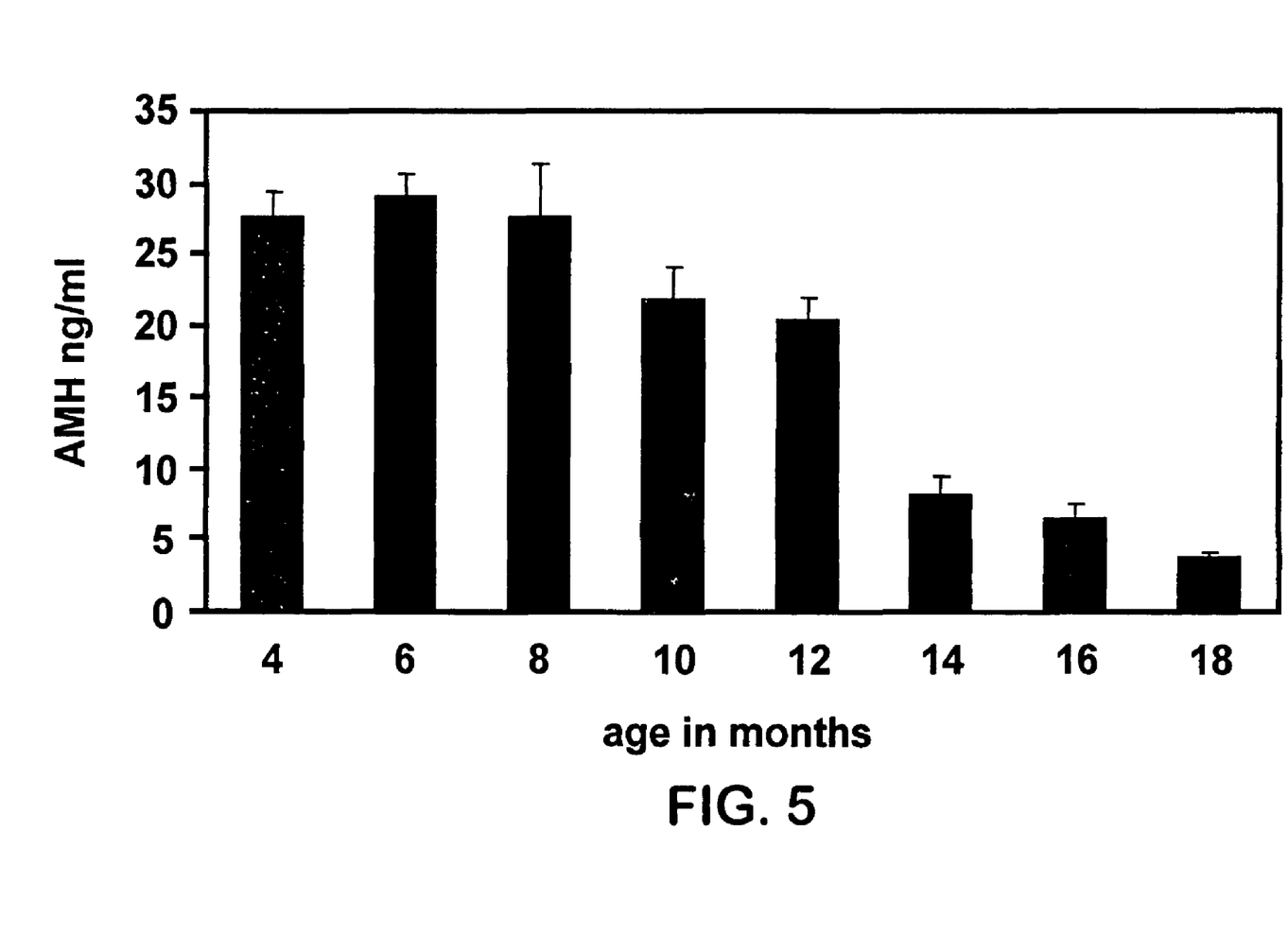
FIG. 5 shows measured AMH levels throughout life in the female mouse by immunoassay using the 12H and 7A antibodies. The results show a decline in serum AMH in female mice with age.

Measurement of decline in serum AMH in mice with age. An assay based on the 12H and 7A antibodies as described herein was employed to determine the level of AMH in mouse sera obtained from aging female mice (see FIG. 5). Mice were killed at different ages on the day of estrous based on vaginal smears. Subsequently, serum samples were subjected to AMH analysis using the assay after 41-fold dilution. Serum AMH levels of 4-, 6- and 8-months-old were not different and were approximately 28.5 ng/ml human standard. Mice aged 10 and 12 months showed decreased AMH levels (22.0 and 20.5 ng/ml human standard. Older mice, 14-, 16- and 18-months-old showed even more decreased AMH levels: 8.2, 6.4 and 3.8 ng/ml human standard, respectively.

Example 9

Figure 6A:
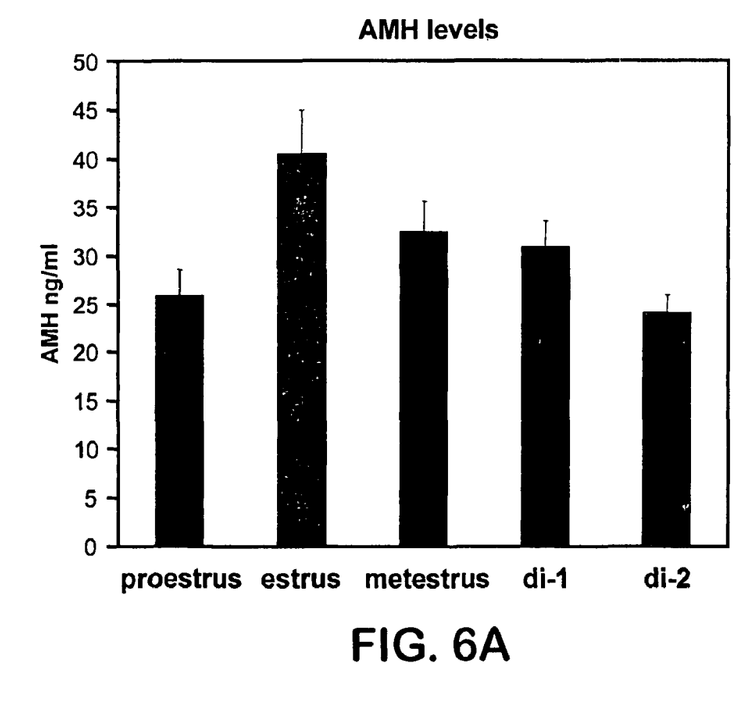
Figure 6B:
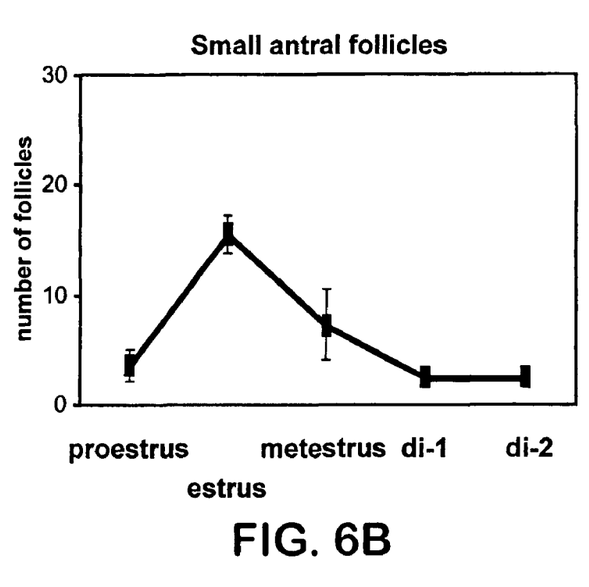

AMH levels throughout the estrous cycle in mice. Four-month-old female mice were classified to different stages of the estrous cycle based on vaginal smears, and post-mortem ovarian follicle analysis. Serum AMH levels were determined using AMH assay based on the antibodies 7A and 12H. Serum AMH levels were stable throughout the estrous cycle at a level of approximately 29 ng/ml human standard, except at estrous when higher levels were found, 40 ng/ml AMH human standard (see FIG. 6A). Preliminary analysis showed correlation of the AMH levels with the number of preantral and small antral follicles in the ovaries of these animals (see FIG. 6B).

Example 10

Measurement of rat AMH in a mouse transgenic background. The assay based on antibodies 7A and 12H was used to determine the levels of rat AMH produced in a mouse transgenic background. Transgenic mice carrying a construct that drives expression of recombinant ratAMH under the control of the PEPCK promoter were killed and AMH was determined in their serum. On the basis of western blot of serum of the transgenic lines, two lines had been identified earlier: the low-expressing line 21 and the high-expressing line 30. The assay based on antibodies 7A and 12H determined AMH levels in these lines as follows: line 21: 9 ng/ml AMH human standard; line 30:70 ng/ml AMH human standard. Both lines are expected to secrete minimal to no endogenous mouse AMH, since their ovaries were devoid of follicles and granulosa cells that produce AMH in the female.

Example 11

Measurement of AMH levels in samples from monkey and bull, using assays described herein. Serum AMH values were determined in female monkeys of various ages and menopausal status, as shown in Table 3.

TABLE 3

Serum AMH measurements in female monkeys.

| Birth year | Status | AMH [ng/ml] |
|---|---|---|
| 1975 | menopausal | 0.89 |
| 1982 | menopausal | 0.24 |
| 1990 | cyclic | 5.71 |

TABLE 3-continued

Serum AMH measurements in female monkeys.

| Birth year | Status | AMH [ng/ml] |
|---|---|---|
| 1990 | cyclic | 19.59 |
| 1990 | cyclic | 11.15 |
| 1990 | cyclic | 1.28 |
| 1990 | cyclic | 9.16 |
| 1990 | cyclic | 4.36 |

Serum AMH levels were also measured in bovine serum samples using assays described herein, as shown in Table 4.

TABLE 4

Serum AMH measurements in bovine samples

| Sample | AMH(ng/ml) |
|---|---|
| ox1 (castrated bull) | 0.00 |
| ox2 (castrated bull) | 0.00 |
| ox3 (castrated bull) | 0.45 |
| youngborn male calf1 | 8.12 |
| youngborn male calf2 | 8.20 |

Example 12

ELISA assay for the quantitative measurement of MIS/AMH in serum. An MIS/AMH ELISA disclosed herein is an enzymatically amplified two-site immunoassay. In the assay, Standards, Controls, and unknown serum samples are incubated in microtitration wells which have been coated with anti-MIS/AMH antibody. After incubation and washing, the wells are treated with another anti-MIS/AMH detection antibody labeled with biotin. After a second incubation and washing step, the wells are incubated with streptavidin-horseradish peroxidase (HRP). After a third incubation and washing step, the wells are incubated with the substrate tetramethylbenzidine (TMB). An acidic stopping solution is then added and the degree of enzymatic turnover of the substrate is determined by dual wavelength absorbance measurement at 450 and 620 nm. The absorbance measured is directly proportional to the concentration of MIS/AMH present. A set of MIS/AMH Standards is used to plot a standard curve of absorbance versus MIS/AMH concentration from which the MIS/AMH concentrations in the unknowns can be calculated.

Reagents

A. Anti-MIS/AMH-Coated Microtitration Strips:

Stripholders with 96 microtitration wells with anti-MIS/AMH IgG immobilized to the inside wall of each well. These were stored at 2-8° C. with a desiccant to protect from moisture.

B. MIS/AMH Sample Diluent:

Sample Diluent containing concentrations of 0 ng/mL MIS/AMH in a protein-based buffer with a non-mercury preservative. Sample diluent was stored at 2-8° C.

C. MIS/AMH Standards:

Standards containing concentrations of approximately 0.025, 0.10, 0.25, 1.5, 7.5, and 15 ng/mL MIS/AMH in a protein-based buffer with a non-mercury preservative. Standards were stored at 2-8° C.

D. MIS/AMH Controls:

Controls were labeled Levels I and II, containing low and high concentrations of MIS/AMH in a protein-based buffer with a non-mercury preservative. Controls were stored at 2-8° C.

E. MIS/AMH Antibody-Biotin Conjugate—RTU:
Biotinylated MIS/AMH antibody in protein-based buffer with a non-mercury preservative, stored at 2-8° C.

F. Streptavidin-Enzyme Conjugate—RTU:
Streptavidin-HRPO (horseradish peroxidase) in a protein-based (BSA) buffer and a non-mercury preservative, Store undiluted at 2-8° C.

G. MIS/AMH Assay Buffer:
Protein-based (BSA)-buffer with a non-mercury preservative, stored at 2-8° C.

H. TMB Chromogen Solution:
A solution of tetramethylbenzidine (TMB) in citrate buffer with hydrogen peroxide, stored at 2-8° C.

I. Wash Concentrate:
Buffered saline with a nonionic detergent, stored at 2-8° C. or room temperature (~25° C.). The Wash Concentrate was diluted 10-fold with deionized water prior to use.

J. Stopping Solution:
A solution of 0.2 M sulfuric acid, stored at 2-8° C. or room temperature (~25° C.). All reagents and samples were allowed to reach room temperature (~25° C.) and mixed thoroughly by gentle inversion before use.

Assay Procedure

All samples and reagents were allowed to reach room temperature (~25° C.) and mixed thoroughly by gentle inversion before use. Standards, Controls, and unknowns were assayed in duplicate.

Protocol:
1. Mark the microtitration strips to be used.
2. Pipette 20 µL of the Standards, Controls and unknowns to the appropriate wells.
3. Add 100 µL of the MIS/AMH Assay Buffer to each well using a semi-automatic dispenser.
4. Incubate the wells, shaking at a fast speed (500-700 rpm) on an orbital microplate shaker, for 1 hour at room temperature (~25° C.).
5. Aspirate and wash each well 5 times with the Wash Solution using an automatic microplate washer, or by aspirating the liquid from each well, dispensing 0.35 mL of the Wash Solution into each well, and aspirating the Wash Solution. Blot dry by inverting plate on absorbent material.
6. Add 100 µL of the Antibody-Biotin Conjugate—RTU to each well using a semi-automatic dispenser.
7. Incubate the wells, shaking at a fast speed (500-700 rpm) on an orbital microplate shaker, for 1 hour at room temperature (~25° C.).
8. Aspirate and wash each well 5 times with the Wash Solution using an automatic microplate washer, or by completely aspirating the liquid from each well, dispensing 0.35 mL of the Wash Solution into each well, and aspirating the Wash Solution. Blot dry by inverting plate on absorbent material.
9. Add 100 µL of the Streptavidin-Enzyme Conjugate—RTU to each well using a semi-automatic dispenser.
10. Incubate the wells, shaking at a fast speed (500-700 rpm) on an orbital microplate shaker, for 30 minutes at room temperature (~25° C.).
11. Aspirate and wash each well 5 times with the Wash Solution using an automatic microplate washer, or by completely aspirating the liquid from each well, dispensing 0.35 mL of the Wash Solution into each well, and aspirating the Wash Solution. Blot dry by inverting plate on absorbent material.
12. Add 100 µL of the TMB Chromogen Solution to each well using a semi-automatic dispenser.
13. Incubate the wells, shaking at a fast speed (500-700 rpm) on an orbital microplate shaker for 15-30 minutes at room temperature (~25° C.). Avoid exposure to direct sunlight.
14. Add 100 µL of the Stopping Solution to each well using a semi-automatic dispenser.
15. Read the absorbance of the solution in the wells within 30 minutes, using a microplate reader set to 450 nm. While reading the absorbance of the microtitration well, it is necessary to program the zero Standard as a "Blank". If wavelength correction is available, set the instrument to dual wavelength measurement at 450 nm with background wavelength correction set at 600 or 620 nm.

Calculation of Results:
1. Calculate the mean absorbance for each Standard, Control, or unknown.
2. Plot the log of the mean absorbance readings for each of the standards along the y-axis versus log of the MIS/AMH concentrations in ng/mL along the x-axis, using a linear curve-fit. Alternatively, the data can be plotted linear vs. linear and a smoothed spline curve-fit can be used.
3. Draw the best fitting curve through the mean of the duplicate points.
4. Determine the MIS/AMH concentrations of the Controls and unknowns from the standard curve by matching their mean absorbance readings with the corresponding MIS/AMH concentrations.

Example 13

Immunoassay measurement of AMH in human serum. The performance characteristics of AMH measurements in human serum by an ELISA assay as described herein, using the 12H and 7A antibodies, are shown below in Table 5 and Table 6. In this example, antibody 12H was used as the capture antibody and antibody 7A was used as the detection antibody. The theoretical sensitivity, or minimum detection limit, as calculated by interpolation of the mean plus two standard deviations of 8 replicates of the 0 ng/mL MIS/AMH Standard, was 0.0058 ng/mL.

Table 5 shows the linearity of dilution of measured amounts of AMH in human serum samples. Recovery is calculated as the percent of the observed concentration divided by the expected concentration.

TABLE 5

Linearity of dilution of AMH measured values in human serum samples using ELISA assay.
Linearity of Dilution

| Sample number Measured AMH value (ng/ml) | Dilution Factor | Expected value (ng/ml) | Observed value (ng/ml) | Percent Recovery |
|---|---|---|---|---|
| I 1.931 | — | — | — | — |
| | 1:2 | 0.965 | 0.997 | 103 |
| | 1:4 | 0.482 | 0.445 | 92 |
| | 1:8 | 0.241 | 0.222 | 92 |
| | 1:16 | 0.120 | 0.096 | 80 |
| | 1:32 | | | |
| II 2.462 | — | | | |
| | 1:2 | 1.231 | 1.225 | 100 |
| | 1:4 | 0.615 | 0.569 | 92.5 |
| | 1:8 | 0.307 | 0.259 | 84 |
| | 1:16 | 0.154 | 0.149 | 97 |
| | 1:32 | | | |
| III 7.650 | — | | | |
| | 1:2 | 3.825 | 4.159 | 109 |
| | 1:4 | 1.912 | 2.097 | 110 |
| | 1:8 | 0.956 | 0.981 | 93 |
| | 1:16 | 0.478 | 0.441 | 92 |
| | 1:32 | | | |

Table 6 shows the intra-assay and inter-assay precision, and recovery characteristics of the assay. The intra-assay precision was determined from the mean of 8 replicates each. Recovery is calculated as the percent of the observed concentration divided by the expected concentration.

TABLE 6

| Sample number | N | Mean (ng/ml) | SD | CV (percent) |
|---|---|---|---|---|
| *Precision (Intra-assay)* | | | | |
| I | 8 | 0.241 | 0.011 | 4.1 |
| II | 8 | 1.422 | 0.038 | 2.7 |
| III | 8 | 7.871 | 0.3 | 3.8 |
| *Precision (Inter-assay)* | | | | |
| I | 10 | 0.236 | 0.0134 | 5.7 |
| II | 10 | 1.415 | 0.106 | 7.4 |
| III | 10 | 7.584 | 0.568 | 7.5 |

| Sample number | Endogenous (ng/ml) | Added (ng/ml) | Expected (ng/ml) | Observed (ng/ml) | Recovery (percent) |
|---|---|---|---|---|---|
| *Recovery* | | | | | |
| I | 1.866 | 1.15 | 2.876 | 2.968 | 103 |
|  |  | 2.3 | 3.886 | 3.540 | 91 |
| II | 2.919 | 1.15 | 3.848 | 4.211 | 109 |
|  |  | 2.3 | 4.777 | 4.972 | 104 |
| III | 4.610 | 1.15 | 5.409 | 5.157 | 95 |
|  |  | 2.3 | 6.208 | 6.548 | 105 |

In Tables 5 and 6 above, "N" means the number of repeated measurements of a sample, "SD" means standard deviation, "CV" means coefficient of variability, "Endogenous" means the amount of AMH measured in the sample before the addition of a known amount of AMH; "Added" means the additional known amount of AMH added to the sample; "Expected" means the expected measured amount of endogenous plus added AMH; "Observed" means the actual measured value of endogenous plus added AMH; and "Recovery" means the percent of the added known amount of AMH that was actually measured by the assay.

Example 14

Immunoassay measurement of AMH in rat serum. An ELISA assay as described herein was performed to measure AMH in rat serum, using the 12H and 7A antibodies. In this example, antibody 12H was used as the capture antibody, and antibody 7A was used as the detection antibody. The performance characteristics of this assay are shown in Tables 7 and 8. Table 7 shows the linearity of dilution of measured amounts of AMH in rat samples measured using an ELISA assay. Rat serum samples were diluted with sample diluent (0 ng/ml AMH) and assayed. Recovery is calculated as the percent of the observed concentration divided by the expected concentration. The theoretical sensitivity of the ELISA assay for rat AMH was 0.012 ng/ml, and was calculated by interpolation of the mean plus two standard deviations of 16 replicated measurements of sample diluent.

TABLE 7

Linearity of dilution of AMH measured values in rat serum samples in ELISA assay

| Sample number | Dilution Factor | Expected | Observed | Recovery (percent) |
|---|---|---|---|---|
| I | — |  | 3.987 |  |
|  | 1:2 | 1.993 | 1.830 | 92 |
|  | 1:4 | 0.997 | 0.902 | 91 |
|  | 1:8 | 0.498 | 0.466 | 94 |
|  | 1:16 | 0.249 | 0.237 | 95 |
| II | — |  | 6.268 |  |
|  | 1:2 | 3.134 | 3.007 | 96 |
|  | 1:4 | 1.567 | 1.530 | 98 |
|  | 1:8 | 0.783 | 0.802 | 102 |
|  | 1:16 | 0.391 | 0.409 | 105 |
| III | — |  | 11.322 |  |
|  | 1:2 | 3.134 | 3.007 | 96 |
|  | 1:4 | 1.567 | 1.530 | 98 |
|  | 1:8 | 0.783 | 0.802 | 102 |
|  | 1:16 | 0.391 | 0.409 | 105 |

Table 8 shows the recovery characteristics of measured amounts of rat AMH in an ELISA assay. Serum samples were spiked with different known amounts of an elevated AMH stock sample and assayed. Recovery is calculated as the percent of the observed value divided by the expected concentration.

TABLE 8

Recovery of known added amounts of rat AMH to rat serum samples in ELISA assay

| Sample number | Endogenous (ng/ml) | Added (ng/ml) | Expected (ng/ml) | Observed (ng/ml) | Recovery (percent) |
|---|---|---|---|---|---|
| I | 1.534 | 2.7 | 3.982 | 4.315 | 108 |
|  |  | 5.4 | 6.430 | 6.376 | 99 |
| II | 3.405 | 2.7 | 5.513 | 5.270 | 95.6 |
|  |  | 5.4 | 7.621 | 7.253 | 95 |
| III | 6.760 | 2.7 | 8.258 | 8.135 | 98.5 |
|  |  | 5.4 | 9.756 | 9.718 | 100 |

The examples provided herein describe compositions and methods effective to measure AMH in a sample, including biological samples, such as human, mouse, rat, bovine and horse samples. Antibodies useful in such compositions and methods are described. Antibodies described herein bind to the mature region of AMH, and recognize epitopes that are stable to proteolysis of AMH, so that the amounts of AMH measured are unaffected by proteolysis of AMH.

The following references are cited herein:

Al-Qahtani, A., Muttukrishna, S., Appasamy, M., Johns, J, Cranfield, M., Visser, J. A., Themmen, A. P. N., Groome, N. P. (2005) Development of a sensitive enzyme immunoassay for Anti-Mullerian Hormone (AMH) and the evaluation of potential clinical applications in males and females. *Clin. Endocrinol.*, 63(3), 267-73.

Baarends, W. M., Uilenbroek, J. T., Kramer, P., Hoogerbrugge, J. W., van Leeuwen, E. C., Themmen, A. P., et al. (1995). *Endocrinology*, 136, 4951-4962.

Cate, R. L. and Pepinsky, R. B., U.S. Pat. No. 5,359,033.

di Clemente, N. et al. (1994). *Mol. Endocrinol.*, 8, 1006-1020.

Durlinger, A. L., Kramer, P., Karels, B., de Jong, F. H., Uilenbroek, J. T., Grootegoed, J. A., et al. (1999). *Endocrinology*, 140, 5789-5796.

GenBank, National Center for Biotechnology Information, www.ncbi.nlm.nih.gov. Homology data derived from AMH gene sequences from the NCBI GenBank public nucleotide sequence database.

Gruijters, M., Visser, J., Durlinger, A., Themmen, A. P. (2003) Anti-Müllerian hormone and its role in ovarian function. *Molecular and Cellular Endocrinology,* 211, 85-90.

Hudson, P., Dougas, I., Donahoe, P., Cate, R., Epstein, J., Pepinsky, R B., MacLaughlin, D. (1990). An immunoassay to detect human Müllerian inhibiting substance in males and females during normal development. *Journal of Clinical Endocrinology and Metabolism,* 70, 16-22.

Lee, M., Donahoe, P. (1993) Müllerian-inhibiting substance: A gonadal hormone with multiple functions. *Endocrine Reviews,* 142, 152-164.

Lee, M., Donahoe, P., Hasegawa, T., Silverman, B., Crist, G., Best, S., Hasegawa, Y., Noto, R., Schoenfeld, D., MacLaughlin, D. (1996) Mullerian Inhibiting Substance in human: normal levels from infancy to adulthood. *Journal of Clinical Endocrinology and Metabolism* 81, 571-575.

Lee, M., Misra, M., Donahoe, P., MacLaughlin, D. (2003) MIS/AMH in the assessment of cryptorchidism and intersex conditions. *Molecular and Cellular Endocrinology,* 211, 91-98.

Long, W. Q., Ranchin, V., Pautier, P., Belville, C., Denizot, P., Cailla, H., Lhomme, C., Picard, J. Y., Bidart. J. M., Rey, R. (2000) Detection of minimal levels of serum anti-Müllerian hormone during follow-up of patients with ovarian granulosa cell tumor by means of a highly sensitive enzyme-linked immunosorbent assay. *Journal of Clinical Endocrinology Metabolism,* 85, 540-544.

Picard, J. Y., et al. (1986). *Proc. Natl. Acad. Sci.,* 83, 5464-5468.

Picon, R. (1969). *Arch. Anat. Microsc. Morphol. Exp.,* 58, 1-19.

te Velde, E., Pearson, P. (2002) The variability of female reproductive ageing. *Human Reproduction. Update,* 8, 141-154.

Teixeira, J. et al. (2001). *Endocrine Reviews,* 22, 657-674.

van Rooij, I. A., Broekmans, F. J., teVelde, E. R., Fauser, B. C., Bancsi, L. F., de Jong, F. H., Themmen, A. P. (2002) Serum anti-Müllerian hormone levels: a novel measure of ovarian reserve. *Human Reproduction,* 17, 3065-3071.

Wilson, C., Di Clemente, N., Ehrenfels, C., Pepinsky, R., Josso, N., Vigier, B., Cate, R. (1993) Müllerian inhibiting substance requires its N-terminal domain for maintenance of biological-activity, a novel finding within the transforming growth-factor-beta superfamily. *Molecular Endocrinology,* 7, 247-257.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition comprising a first antibody and a second antibody, wherein the first antibody binds to a first epitope in a mature region of an Anti-Mullerian Hormone and the second antibody binds to a second epitope in the mature region of the Anti-Mullerian Hormone.

2. The composition of claim 1, wherein the first antibody and the second antibody comprise monoclonal antibodies.

3. The composition of claim 1, further comprising a solid support bound to the first antibody.

4. The composition of claim 3, wherein the solid support comprises a protein binding surface selected from the group consisting of a microtiter plate, a colloidal metal particle, an iron oxide particle, a latex particle and a polymeric bead.

5. The composition of claim 1, further comprising the second antibody coupled with a label.

6. The composition of claim 5, wherein the label comprises a chemiluminescent agent, a colorimetric agent, an energy transfer agent, an enzyme, a fluorescent agent or a radioisotope.

7. The composition of claim 1, wherein the Anti-Mullerian Hormone comprises a mammalian Anti-Mullerian Hormone selected from the group consisting of primate, rodent, equine, and bovine Anti-Mullerian Hormone.

8. The composition of claim 7, wherein the primate Anti-Mullerian Hormone comprises a human Anti-Mullerian Hormone, and the rodent Anti-Mullerian Hormone comprises a mouse or a rat Anti-Mullerian Hormone.

9. A method for measuring an amount of an Anti-Mullerian Hormone in a sample containing Anti-Mullerian Hormone comprising:
   (a) binding a first antibody to an Anti-Mullerian Hormone, wherein the first antibody binds to a first epitope in a mature region of the Anti-Mullerian Hormone;
   (b) binding a second antibody to the Anti-Mullerian Hormone, wherein the second antibody binds to a second epitope in the mature region of the Anti-Mullerian Hormone, thereby creating an amount of bound second antibody;
   (c) measuring the amount of bound second antibody; and
   (d) calculating the amount of Anti-Mullerian Hormone in the sample.

10. The method of claim 9, further comprising a solid support bound to the first antibody.

11. The method of claim 10, wherein the solid support comprises a protein binding surface selected from the group consisting of a microtiter plate, a colloidal metal particle, an iron oxide particle, a latex particle and a polymeric bead.

12. The method of claim 9, further comprising a label coupled with the second antibody.

13. The method of claim 12, wherein the label comprises a chemiluminescent agent, a colorimetric agent, an energy transfer agent, an enzyme, a fluorescent agent or a radioisotope.

14. The method of claim 9, wherein the Anti-Mullerian Hormone comprises a mammalian Anti-Mullerian Hormone selected from the group consisting of primate, rodent, equine, and bovine Anti-Mullerian Hormone.

15. A composition for measuring an amount of Anti-Mullerian Hormone in a sample comprising:
   (a) a first antibody and a second antibody that bind to a mature region of an Anti-Mullerian Hormone, wherein the first antibody binds to a first epitope in a mature region of the Anti-Mullerian Hormone and the second antibody binds to a second epitope in the mature region of the Anti-Mullerian Hormone;
   (b) a solid support coupled with the first antibody; and
   (c) a label coupled with the second antibody.

16. The composition of claim 15, wherein the Anti-Mullerian Hormone comprises a mammalian Anti-Mullerian Hormone selected from the group consisting of primate, rodent, equine, and bovine Anti-Mullerian Hormone.

17. The composition of claim 15, wherein the solid support comprises a protein binding surface selected from the group consisting of a microtiter plate, a colloidal metal particle, an iron oxide particle, a latex particle and a polymeric bead.

18. The composition of claim 15, wherein the label comprises a chemiluminescent agent, a colorimetric agent, an energy transfer agent, an enzyme, a fluorescent agent or a radioisotope.

* * * * *